US012714652B2

(12) United States Patent
Klee et al.

(10) Patent No.: US 12,714,652 B2
(45) Date of Patent: Aug. 25, 2026

(54) DENTAL IMPRESSION MATERIAL

(71) Applicant: DENTSPLY SIRONA Inc., York, PA (US)

(72) Inventors: Joachim Klee, Radolfzell (DE); Florian Szillat, Constance (DE); Marjorie Yon, Villelongue de la Salanque (FR); Jurgen H Fiedler, Allensbach (DE); Jacques Lalevee, Mulhouse (FR); Julie Kirschner, Dambach-la-Ville (FR); Laura Perrard, Auchel (FR)

(73) Assignee: Dentsply Sirona Inc., York, PA (US)

( * ) Notice: Subject to any disclaimer, the term of this patent is extended or adjusted under 35 U.S.C. 154(b) by 0 days.

(21) Appl. No.: 18/420,008

(22) Filed: Jan. 23, 2024

(65) Prior Publication Data

US 2024/0342060 A1 Oct. 17, 2024

Related U.S. Application Data

(63) Continuation of application No. 16/755,039, filed as application No. PCT/EP2018/077425 on Oct. 9, 2018, now abandoned.

(30) Foreign Application Priority Data

Oct. 13, 2017 (EP) .................................... 17196314

(51) Int. Cl.
*C08L 83/04* (2006.01)
*A61K 6/62* (2020.01)
*A61K 6/90* (2020.01)
*C08G 77/08* (2006.01)
*C08G 77/20* (2006.01)
*C08K 5/45* (2006.01)

(52) U.S. Cl.
CPC .................. *A61K 6/90* (2020.01); *A61K 6/62* (2020.01); *C08L 83/04* (2013.01); *C08G 77/08* (2013.01); *C08G 77/20* (2013.01); *C08K 5/45* (2013.01)

(58) Field of Classification Search
CPC ............ A61K 6/90; C08L 83/04; C08G 77/08
USPC ............................................ 525/478; 528/15
See application file for complete search history.

(56) References Cited

U.S. PATENT DOCUMENTS 3,775,452 A 11/1973 Karstedt
4,510,094 A 4/1985 Drahnak
4,600,484 A 7/1986 Drahnak
4,916,169 A * 4/1990 Boardman ............... C08K 5/56 522/69
5,145,886 A 9/1992 Oxman et al.
5,187,015 A 2/1993 Yorkgitis et al.
5,403,885 A 4/1995 Voigt et al.
6,376,569 B1 4/2002 Oxman et al.
6,747,071 B1 * 6/2004 Frances .................... A61K 6/62 522/170
2006/0281856 A1 12/2006 Kollefrath et al.
2008/0033071 A1 * 2/2008 Irmer ...................... C08L 83/04 522/66
2010/0256300 A1 10/2010 Jandke et al.
2014/0170596 A1 6/2014 Angeletakis
2016/0319086 A1 * 11/2016 Pouget ....................... C08J 3/28
2021/0186825 A1 6/2021 Klee et al.

FOREIGN PATENT DOCUMENTS

CA 3076264 1/2023
EP 0358452 A2 3/1990
EP 0398701 A2 11/1990
EP 3470049 A1 4/2019
EP 3694467 8/2020
JP H02107669 A 4/1990
JP H0328269 A 2/1991
JP H092916 A 1/1997
JP 2008508382 A 3/2008
JP 2016079190 A 5/2016
JP 2017057270 A 3/2017
WO WO-9826748 A2 6/1998
WO WO-2019072816 A1 4/2019

OTHER PUBLICATIONS

"U.S. Appl. No. 16/755,039, Final Office Action mailed Jul. 31, 2023", 10 pgs.
"U.S. Appl. No. 16/755,039, Non Final Office Action mailed Jan. 24, 2023", 11 pgs.
"U.S. Appl. No. 16/755,039, Preliminary Amendment filed Apr. 9, 2020", 4 pgs.
"U.S. Appl. No. 16/755,039, Response filed May 9, 2023 to Non Final Office Action mailed Jan. 24, 2023", 14 pgs.
"U.S. Appl. No. 16/755,039, Response filed Nov. 22, 2022 to Restriction Requirement mailed Jul. 26, 2022", 2 pgs.
"U.S. Appl. No. 16/755,039, Restriction Requirement mailed Jul. 26, 2022", 4 pgs.
"European Application Serial No. 17196314.3, Extended European Search Report mailed Apr. 20, 2018", 7 pgs.
"European Application Serial No. 17196314.3, Noting of loss of rights pursuant to Rule 112(1) EPC mailed Nov. 5, 2019", 2 pgs.
"International Application Serial No. PCT/EP2018/077425, International Preliminary Report on Patentability mailed Apr. 23, 2020", 9 pgs.

(Continued)

*Primary Examiner* — Margaret G Moore
(74) *Attorney, Agent, or Firm* — SCHWEGMAN LUNDBERG & WOESSNER, P.A.

(57) ABSTRACT

The present invention relates to a dental impression material adapted to be cured by visible light, comprising a compound having one or more aliphatic unsaturated groups, a compound containing at least one silicon-bonded hydrogen atom and not having more than three hydrogen atoms attached to any one silicon atom, a photoactivatable catalyst component, and a specific initiator component.

10 Claims, 6 Drawing Sheets

(56) References Cited

OTHER PUBLICATIONS

"International Application Serial No. PCT/EP2018/077425, International Search Report mailed Dec. 17, 2018", 4 pgs.
"International Application Serial No. PCT/EP2018/077425, Written Opinion mailed Dec. 17, 2018", 7 pgs.
"Japanese Office Action dated Jul. 13, 2021".
"Canadian Application Serial No. 3,076,264, Examiners Rule 862 Report mailed Nov. 30, 2021", 4 pgs.
"Canadian Application Serial No. 3,076,264, Response filed Mar. 30, 2022 to Examiners Rule 862 Report mailed Nov. 30, 2021", w English Claims, 14 pgs.
"Canadian Application Serial No. 3,076,264, Voluntary Amendment filed Dec. 17, 2020", w English Claims, 11 pgs.
"European Application Serial No. 18783478.3, Response to Communication pursuant to Rules 1611 and 162 EPC filed Nov. 20, 2020", W English Claims, 5 pgs.
"European Application Serial No. 18783478.3, Communication Pursuant to Article 943 EPC mailed May 17, 2021", 5 pgs.
"European Application Serial No. 18783478.3, Response filed Nov. 26, 2021 to Communication Pursuant to Article 943 EPC mailed May 17, 2021", W English Claims, 5 pgs.
"European Application Serial No. 18783478.3, Communication Pursuant to Article 943 EPC mailed Mar. 31, 2023", 5 pgs.
"European Application Serial No. 18783478.3, Response filed May 8, 2023 to Communication Pursuarit to Article 943 EPC mailed Mar. 31, 2023", W English Claims, 10 pgs.

* cited by examiner

*cis*-Pt(L)$_2$ *trans*-Pt(L)$_2$

| Pt(L)$_2$ | $R_1$ | $R_2$ |
|---|---|---|
| Pt(acac)$_2$ | $CH_3$ | $CH_3$ |
| Pt(dbm)$_2$ | $C_6H_5$ | $C_6H_5$ |
| Pt(bac)$_2$ | $C_6H_5$ | $CH_3$ |
| Pt(btfac)$_2$ | $C_6H_5$ | $CF_3$ |
| Pt(tfac)$_2$ | $CH_3$ | $CF_3$ |
| Pt(hfac)$_2$ | $CF_3$ | $CF_3$ |

DENTAL IMPRESSION MATERIAL

This application is a CON of U.S. Ser. No. 16/755,039 filed Apr. 9, 2020 and now abandoned. Ser. No. 16/755,039 is a 371 application of PCT/EP2018/077425 which claims priority to EP 17196314.3 filed Oct. 13, 2017.

FIELD OF THE INVENTION

The present invention relates to a dental impression material adapted to be cured by light having a wavelength in the range of from 200 to 800 nm. The dental impression material comprises a compound having one or more aliphatic unsaturated groups, a compound containing at least one silicon-bonded hydrogen atom and not having more than three hydrogen atoms attached to any one silicon atom, a photoactivatable metal catalyst component, a retarder and optionally a specific photosensitizer component. Specifically, the dental impression material of the present invention cures by a photohydrosilylation process.

The dental impression material according to the present invention may be provided as a storage stable two-pack composition. Irradiation of the composition provides a dental impression having mechanical properties suitable for the preparation of indirect dental restorations.

BACKGROUND OF THE INVENTION

A dental impression is a negative imprint of hard teeth and soft dental tissues. The dental impression is used for preparing a positive reproduction of the teeth and soft tissues.

For this purpose, a container filled with a dental impression material having a suitable liquid to semi-solid/ductile consistency is placed over the dental arches. Then, the dental impression material is cured, leaving a negative imprint. Curing may be initiated by admixing two or more components of the dental impression material. Alternatively or additionally, curing may be initiated by irradiation with light.

Among the current dental impression materials, one popular type is based on curable compounds containing one or more silicon atoms, such as silanes and/or siloxanes, typically polyorganosiloxanes (silicones).

WO 93/26748 A2 discloses a polymerizable polyorganosiloxane composition for making a dental impression, comprising: a) a QM resin containing vinyl groups, b) a linear vinyl terminated polydimethyl-siloxane fluid, forming with said QM resin a dispersion having a vinyl content of about 0.16 to 0.24 m-mole/g, c) an organohydrogen polysiloxane for cross-linking said vinyl groups, and d) an organoplatinum catalyst complex for accelerating polymerization. The QM resin is a polyorganosiloxane resin comprising units of $SiO_{4/2}$ and units of $R_x(R_y)_2SiO_{1/2}$, wherein $R_x$ is unsaturated, preferably vinyl, and $R_y$ is alkyl or aryl. The organoplatinum catalyst complex is a catalyst useful for catalyzing the reaction of the silicone atoms (bonded to hydrogen atoms) to the vinyl groups. The preferred organoplatinum catalyst complex is a complex or salt of platinum metal alone or in combination with other noble metals including palladium, rhodium. As most preferred organoplatinum catalyst complex, chloroplatinic acid ($H_2PtCl_6$), preferably in admixture or complex with one or more vinyl materials such as vinylpolysiloxanes (e.g. tetramethyldivinyldisiloxane) is disclosed. Curing of the polymerizable polyorganosiloxane composition is initiated by admixing a paste of the organoplatinum catalyst complex with the residual components of the composition. WO 93/26748 A2 is silent on an adaption of the composition to be cured by irradiation with light.

EP 0 398 701 A2 and U.S. Pat. No. 5,145,886 A discloses a polysiloxane composition prepared by a hydrosilylation process involving the reaction of a compound containing silicon-bonded hydrogen with a compound containing aliphatic unsaturation in the presence of a platinum (II) β-diketonate complex catalyst under actinic radiation having a wavelength of 200 to 800 nm. In the experimental examples, the composition is cured by irradiation with light having a wavelength of about 366 nm, or a wavelength within the range of from 400 to 500 nm, and cure depth based on the irradiation time was determined. It is disclosed that the polysiloxane composition may be used among others for preparing dental impressions. JP 2017-57270 A discloses a composition for preparing a dental prosthesis, which composition comprises a (meth) acrylic group-containing organopolysiloxane, which residues $R_1$ to $R_{n+7}$ are organic groups or siloxane chains, at least one of which is a (meth) acrylic group". JP 2017-57270 A does not disclose a compound having silicon-bonded hydrogen or a compound for catalyzing a hydrosilation reaction.

U.S. Pat. No. 5,403,885 A discloses a transparent fast-curing polysiloxane addition-crosslinking composition comprising a linear organopolysiloxane, an organohydrogenpolysiloxane, and a catalyst for accelerating addition reaction. The linear organopolysioxane may comprise a vinyl radical, but does not contain a hydrogen atom bonded to a silicon atom, and the organohydrogenpolysiloxane is a polydimethylsiloxande having hydrogen atoms on at least two silicone atoms in its molecule. The catalyst is a platinum complex prepared from hexachloroplatinic acid, specifically a complex of platinum and divinyltetramethyldisiloxane.

JP 09-002916 A discloses a core material consisting of silicone rubber hardened and obtained by the reaction of a vinyl group and a hydrosilyl group. The vinyl group is provided by a polyorganosiloxane, and the hydrosilyl group by a polyorgano hydrogen siloxane. The catalyst for reacting vinyl and hydrosilyl groups is a platinum compound representing a resultant of chloroplatinic acid and alcohol, a platinum-olefin complex, a platinum-vinyl siloxane complex, specifically a platinum-vinyl siloxane complex prepared by reacting chloroplatinic acid with 1,3-divinyl-1,1,3,3-tetramethyl disiloxane.

In U.S. Pat. No. 5,403,885 A and JP 09-002916 A, the catalysts for initiating hydrosilation reaction are not photoactivatable. Rather, these documents disclose that hydrosilation reaction is initiated by admixing two or more parts or the compositions.

EP0358452 discloses a hydrosilation process involving the reaction of a compound containing silicon-bonded hydrogen with a compound containing aliphatic unsaturation. Platinum complexes are used for initiating a visible radiation activated hydrosilation reaction. EP0358452 suggests improved detail prepared from a dental impression by painting and irradiating a visible light curable polyvinylsiloxane formulation on a tooth and immediately following the irradiation step, applying a two-part chemically curable impression material by syringe directly over the several teeth both adjacent to and including those previously irradiated with light. EP0358452 does not disclose the preparation of a dental impression without using an additional two-part chemically curable impression material.

SUMMARY OF THE INVENTION

It is the problem of the present invention to provide a dental impression material adapted to be cured by light having a wavelength in the range of from 200 to 800 nm, which dental impression material is improved as compared to conventional dental impression materials based on curable compounds containing one or more silicon atoms and adapted to be cured by visible light. In particular, the present dental impression material is improved in view of the following characteristics:

Polymerization efficiency is improved in terms of a high conversion and good curing rate, depth of cure is improved, and preferably, in addition, mechanical properties, such as tensile strength and tear strength, are improved.

Moreover, it is the problem of the present invention to provide a method for preparing the dental impression material according to the invention, and to further provide a use of the dental impression material according to the invention for the preparation of a dental impression, in particular without using a two-part chemically curable impression material.

The present invention provides a dental impression material adapted to be cured by light in the range of from 200 to 800 nm, comprising:

(i) a compound having one or more aliphatic unsaturated groups;

(ii) a compound containing at least one silicon-bonded hydrogen atom and not having more than three hydrogen atoms attached to any one silicon atom;

(iii) a particulate filler;

(iv) a photoactivatable metal catalyst component;

(v) a retarder, and (vi) optionally a photosensitizer.

Furthermore, the present invention provides a method for preparing a dental impression, which method comprises (a) providing a dental impression material according to the present invention;

(b) taking an impression of a dental structure; and (c) curing the impression material with light having a wavelength in the range of 200 to 800 nm.

Finally, the present invention provides a use of the dental impression material according to the present invention for the preparation of a dental impression, in particular without using a two-part chemically curable impression material.

The present invention is based on the recognition that a dental impression material according to the present invention comprising components (i) to (v) and optionally (vi) provides improved polymerization efficiency in terms of a high conversion and good curing rate, an improved depth of cure, preferably in addition with improved mechanical properties such as tensile strength and tear strength.

Curve (1): Exposure to light starts at t=100 s; and curve (2): Exposure to light starts at t=600 s.

Figure 1:
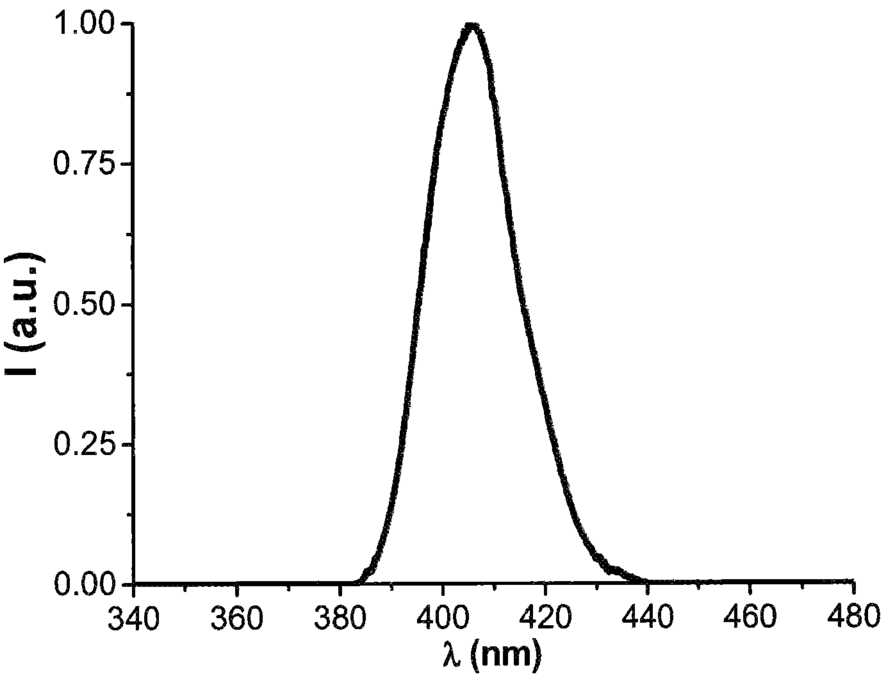
FIG. 1 shows the emission spectra of the irradiation source used for the irradiation of the photocurable samples, namely a light emitting diode (LED) centred at 405 nm (M405L2 from ThorLab; about 110 W/$cm^2$).
Figure 2A:
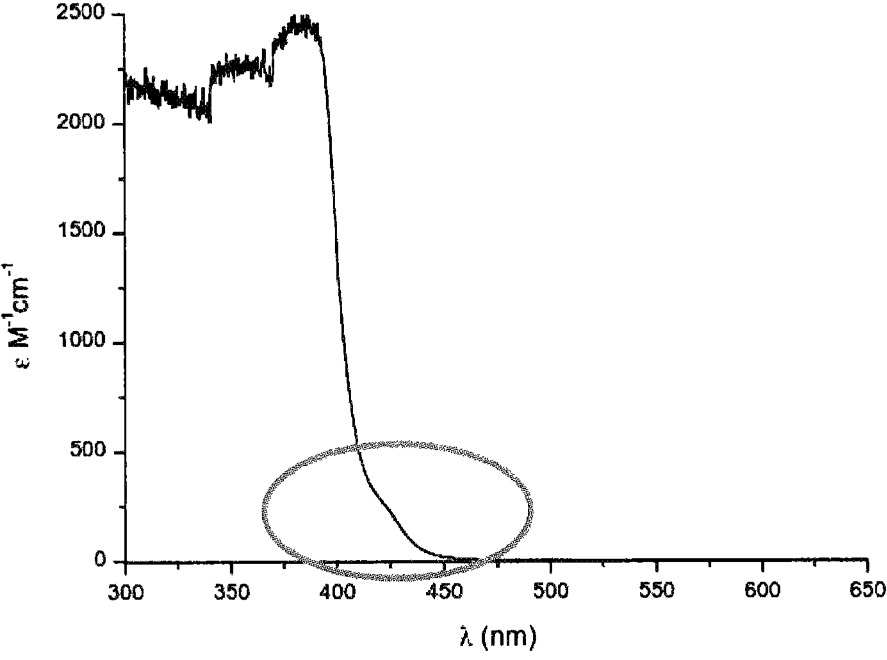
FIGS. 2*a*, 2*b* and 2*c* show the UV-VIS absorption spectra of platinum acetylacetonate ($Pt(acac)_2$), trimethyl(methylcyclopentadienyl)platinum(IV) ($MeCpPt(Me)_3$), and platinum (0)-1,3,divinyl-tetramethyldisiloxane complex solution in vinyl terminated poly(dimethylsiloxane) (Karstedt's catalyst).
Figure 2B:
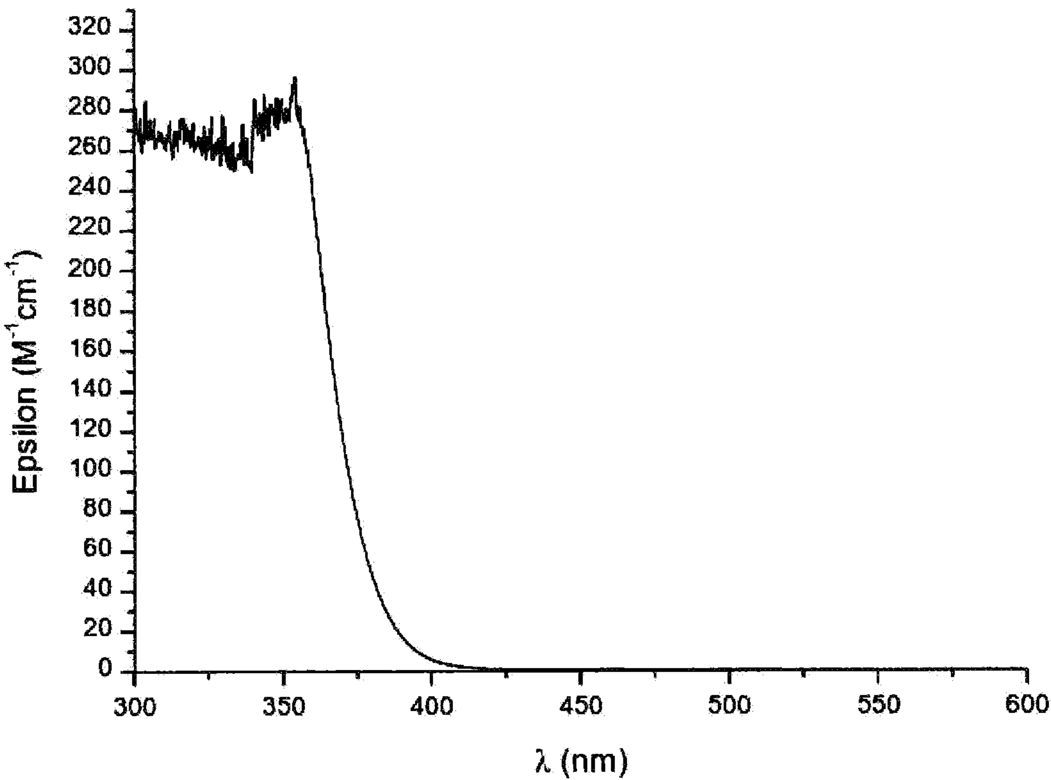
Figure 2C:
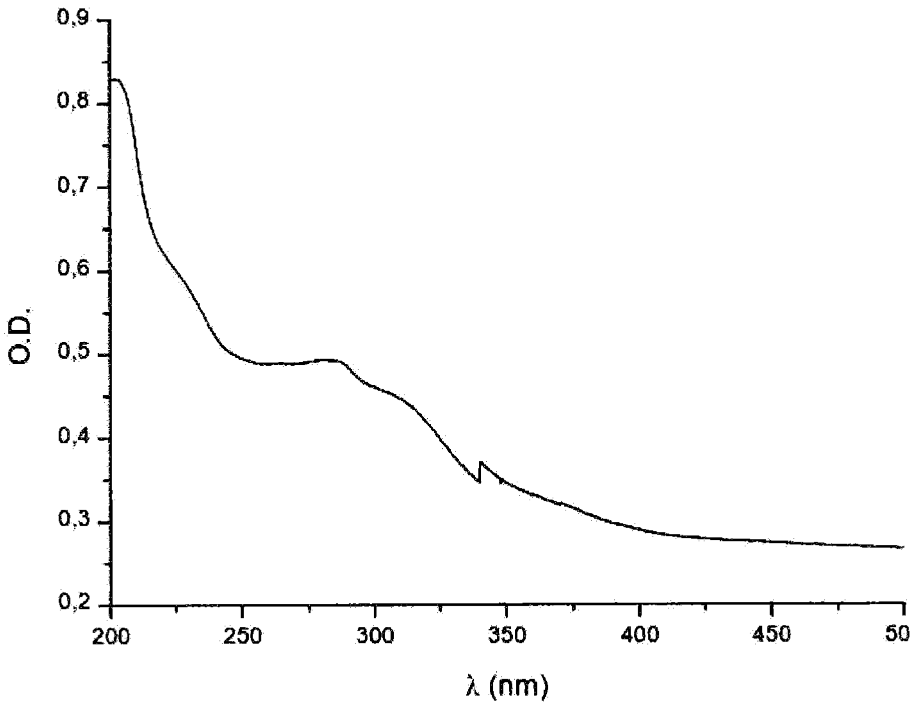
Figure 3:
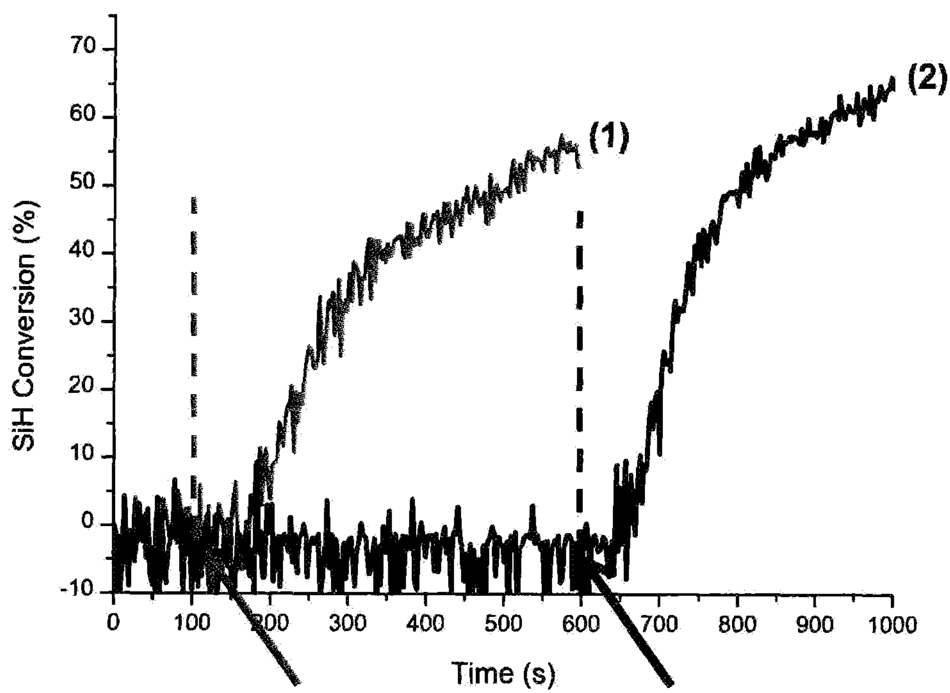
FIG. 3 shows that hydrosilylation of a siloxane liquid in the presence of the photoactivatable catalyst component $Pt(acac)_2$ alone only starts upon exposure to light (LED at 405 nm), and that there is an inhibition of about 50 s from the start time of exposure to light until polymerization starts.
Figure 4:
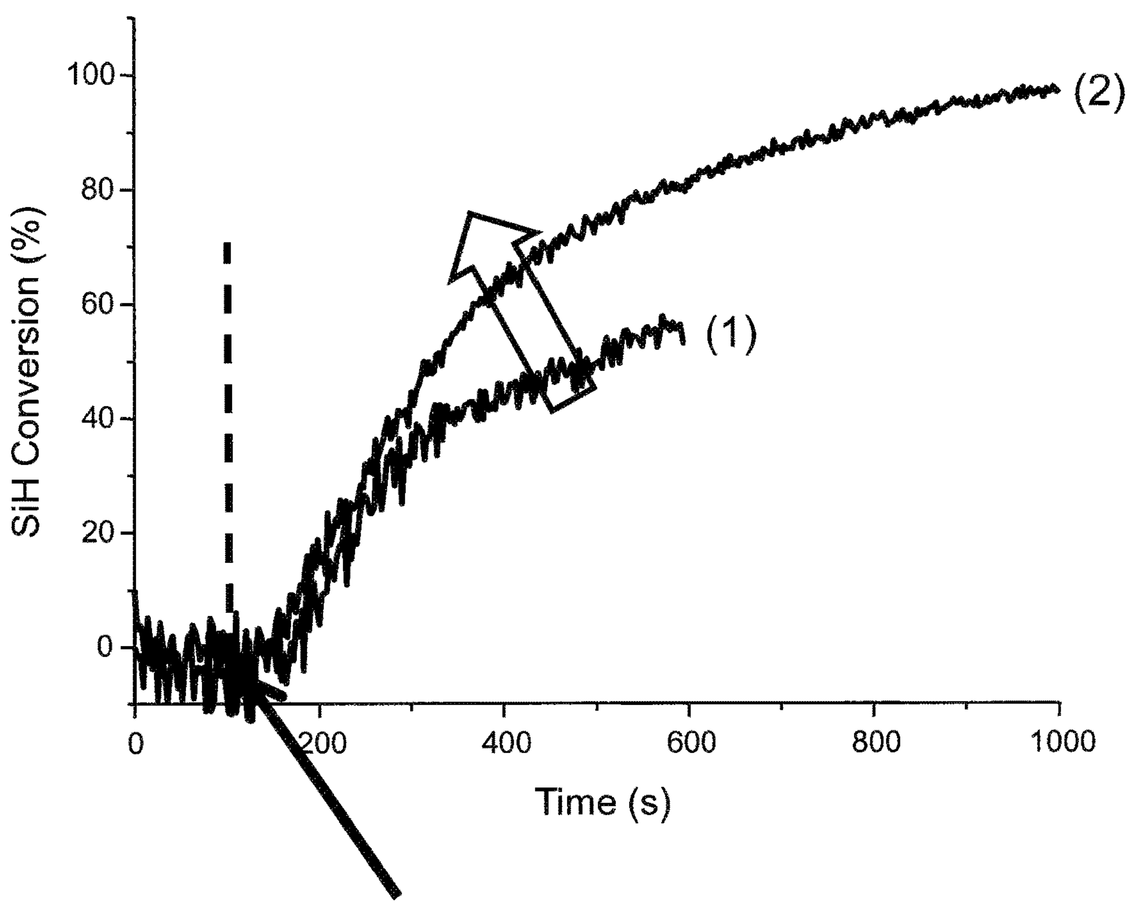

FIG. 4 shows the hydrosilylation profiles of a siloxane liquid upon the exposure to LED at 405 nm for the following photoactivatable catalyst component:

Curve (1): $Pt(acac)_2$ (0.067% w/w); and curve (2): $Pt(acac)_2$ and 9,10-dibutoxyanthracene (DBA).

Figure 5:
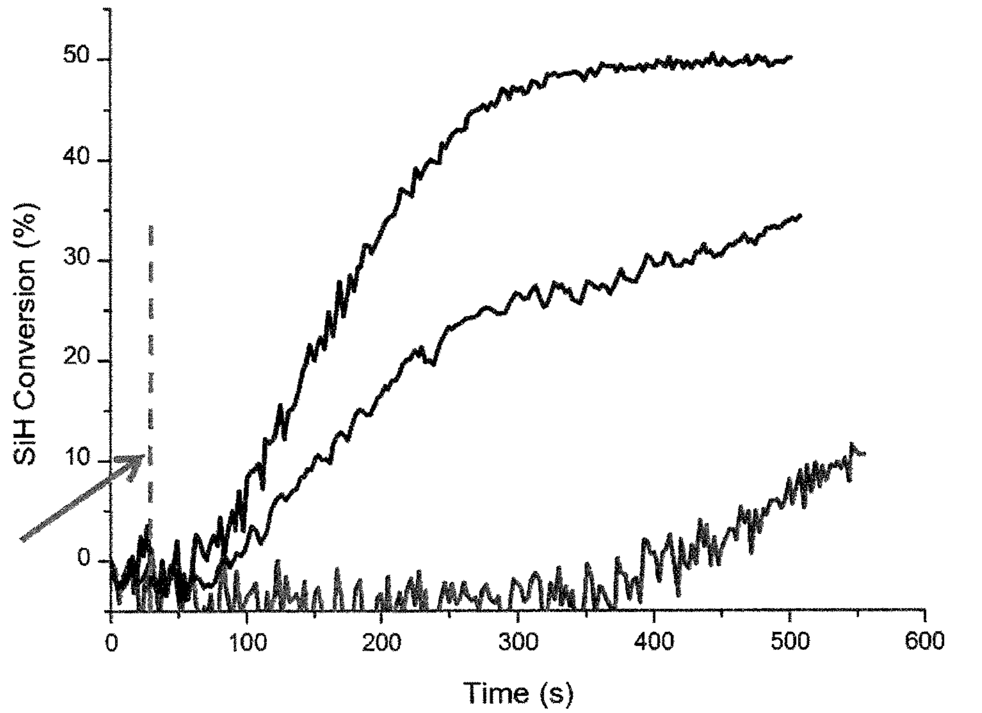

FIG. 5 shows the hydrosilylation profiles of a siloxane liquid upon the exposure to LED at 405 nm for the following photoactivatable catalyst component:

Curve (1): $Pt(acac)_2$ (0.011% w/w) and 2-(diphenylphosphino)benzoic acid (2dppba) (0.011% w/w) in 1,3-dioxolane (4.6% w/w);

curve (2)=reference: Pt(acac)2 (0.011% w/w) in 1,3-dioxolane (4.6% w/w); and curve (3): Pt(acac)2 (0.0095% w/w) and 1-ethynyl-1-cyclohexanol (ECH) (0.005% w/w) in 1,3-dioxolane (4.6% w/w).

Figure 6:
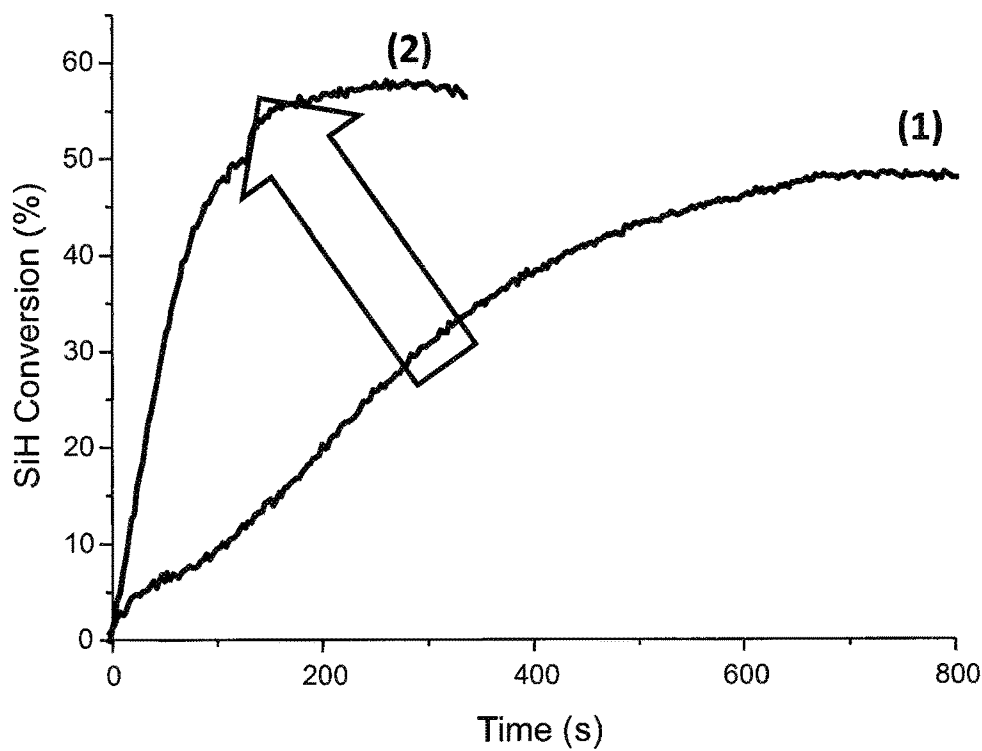

FIG. 6 shows the hydrosilylation profiles of a siloxane liquid under the following conditions:

Curve (1): Photoactivatable catalyst component is only Karstedt's catalyst solution, no exposure to light; and curve (2): Photoactivatable catalyst component is Karstedt's catalyst solution and 2-isopropylthioxanthone (ITX), exposure to LED at 405 nm.

Figure 7:
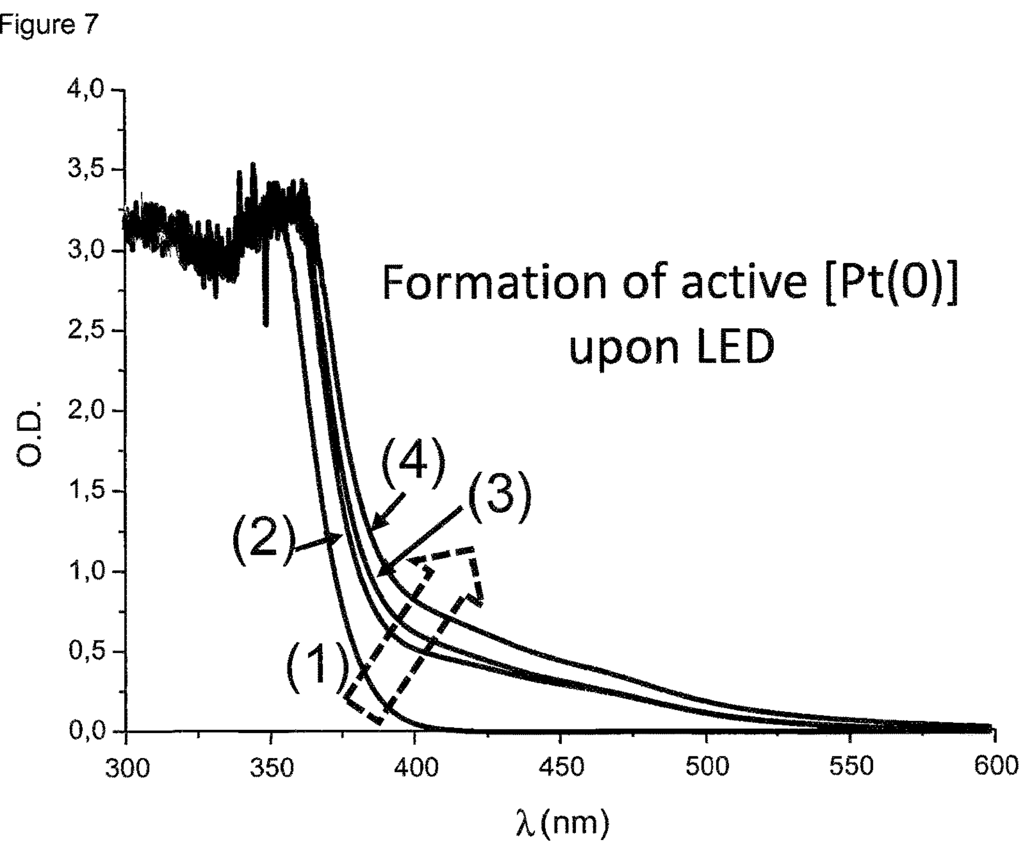

FIG. 7 shows photolysis of $MeCpPt(Me)_3$ in toluene upon exposure to LED at 405 nm for the following periods of time:

Curve (1): 0 s;

curve (2): 30 s;

curve (3): 40 s; and curve (4): 120 s.

Figure 8A:
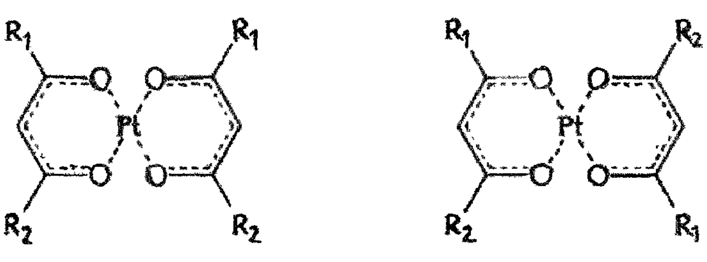
Figure 8B:
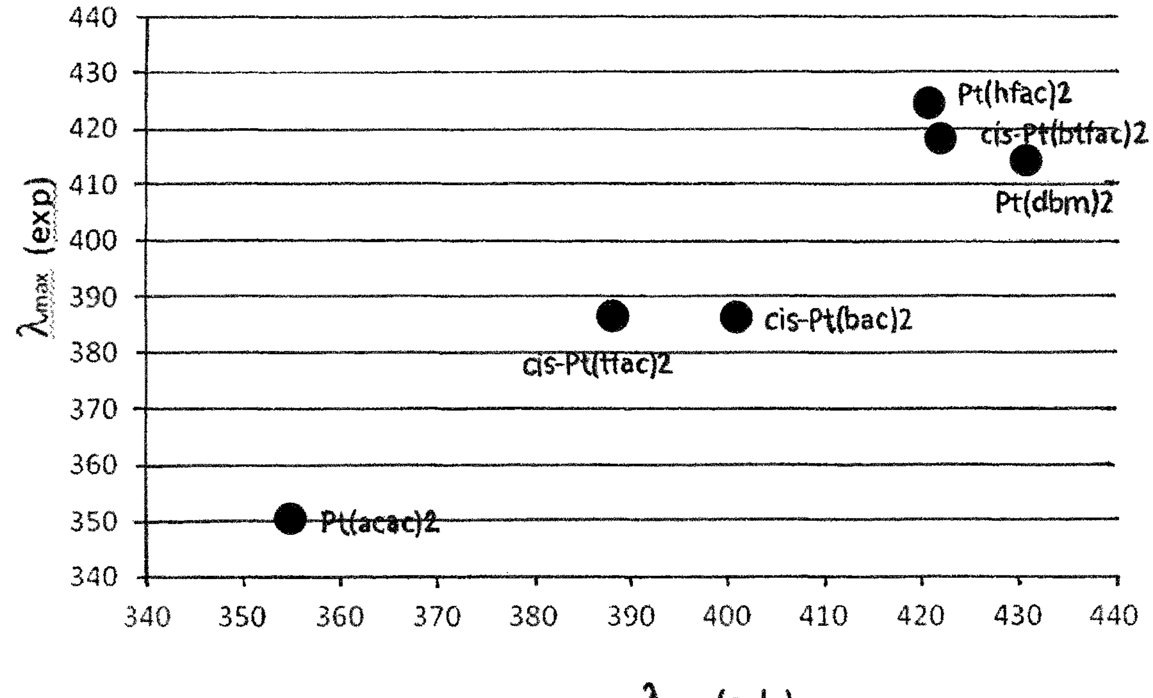

FIGS. 8*a* and 8*b* show the light absorption properties of different platinum complexes which structures are shown in FIG. 8*a*, wherein in FIG. 8*b*, calculated and experimentally determined absorption maximas $\lambda_{max}$ [nm] are plotted against each other.

DETAILED DESCRIPTION OF PREFERRED EMBODIMENTS

The term "adapted to be cured by light" as used herein means that in the present dental impression material, between compounds according to (i) and (ii), a reaction, preferably a polymerization, is initiated when irradiated with light having a wavelength of from 200 to 800 nm, preferably by visible light having a wavelength in the range of from 400 to 800 nm. The reaction between compounds according to (i) and (ii) initiated upon irradiation with light is primarily effected by a hydrosilylation reaction between compound according to (i) and compound according to (ii). The term "hydrosilylation reaction" means an addition reaction of a silane, such as the compound according to (ii), across an unsaturated bond, e.g. of the compound according to (i), whereby a Si—C bond is formed.

The hydrosilylation reaction is initiated by activation of the photoactivatable catalyst component (iv) upon irradiation with visible light. The reaction between compounds according to (i) and (ii) results in a combining by covalent bonding of a large number of the relative small molecules of compounds according to (i) and (ii), to form larger molecules, preferably macromolecules such as oligomers or polymers. The compounds according to (i) and (ii) may be combined to form only linear (macro)molecules, or they may be combined to form three-dimensional macromolecules, commonly referred to as crosslinked polymers.

The term "aliphatic unsaturated groups" used in connection with compound according to (i) means any organic group containing one or more carbon-carbon double or triple bonds, for example alkenyl and alkynyl groups such as a vinyl group or an ethynyl group.

The term "photoactivatable metal catalyst component" encompasses any metal compound that catalyses a hydrosilylation reaction between the compounds according to (i) and (ii) when activated by exposure to light, preferably visible light. The term "visible light" encompasses light having a wavelength within the range of from about 400 nm to about 800 nm.

The term "photosensitizer" encompasses any chemical compound that forms free radicals when activated, by exposure to light alone or in interaction with an electron donor compound in a photochemical process. The photosensizer according to (vi) may act as a coinitiators for the photoactivatable metal catalyst component according to (iv), thereby further improving the curing rate of the hydrosilylation reaction.

The present invention relates to a dental impression material. The dental impression material may be used for preparing dental restorations such as fillings, dental prosthesis, orthodontics, or any other intraoral or extra-oral maxillofacial prosthetics.

The Compounds According to (i) and (ii)

The present dental impression material comprises (i) a compound having one or more aliphatic unsaturated groups. The dental impression material may comprise one or a mixture of two or more compound(s) having one or more aliphatic unsaturated groups (i).

Preferably, the compound having one or more aliphatic unsaturated groups is a compound having a molecular weight of more than 5000 Da.

The term "aliphatic unsaturated group" used in connection with the compound according to (i) means a linear, branched or cyclic alkenyl or alkynyl group. Preferably, the aliphatic unsaturated group is a linear $C_{2-18}$ or branched or cyclic $C_{3-18}$ alkenyl group or linear $C_{2-18}$ or branched $C_{4-18}$ alkynyl group, more preferably a linear $C_{2-12}$ or branched or cyclic $C_{3-12}$ alkenyl group, most preferably a linear $C_{2-6}$ or branched or cyclic $C_{3-6}$ alkenyl group. The alkenyl or alkynyl group may optionally be substituted with one or more halogen atom(s) (F, Cl, Br, I).

In the compound according to (i), the aliphatic unsaturated group is preferably selected from the group consisting of vinyl, chlorovinyl, propenyl and 5-hexenyl, and most preferably, the aliphatic unsaturated group is vinyl.

The compound having one or more aliphatic unsaturated groups (i) may be a linear, branched or cyclic hydrocarbon compound, a linear or branched silane, or a linear, branched or cyclic organic siloxane.

Linear, branched or cyclic hydrocarbon compounds having one or more aliphatic unsaturated groups are preferably alkenes or alkynes. Preferred are linear $C_{2-30}$ or branched or cyclic $C_{3-30}$ alkenes or $C_{2-30}$ or branched $C_{4-30}$ alkynes, more preferably linear $C_{2-20}$ or branched or cyclic $C_{3-20}$ alkenes, most preferably linear $C_{2-8}$ or branched or cyclic $C_{3-8}$ alkenes. These alkenes or alkynes may optionally contain an aromatic group, such as benzene, and/or a heteroatom, preferably an oxygen atom or a nitrogen atom, more preferably oxo-ether group(s), carboxylic acid ester groups or nitrile group(s). Furthermore, such hydrocarbon compounds may be substituted by one or more halogen atom (F, Cl, Br, I).

For example, preferred hydrocarbon compounds are hexene, heptene or octen, 1,5-hexadiene, cyclohexene and cycloheptene, divinylbenzene, methylvinyl ether, divinylether, phenylvinyl ether, monoallyl ether of ethylene glycol, allyl aldehyde, methylvinyl ketone, phenylvinyl ketone, (meth)acrylic acid, methyl (meth)acrylate, allyl (meth)acrylate, vinylacetic acid, vinyl acetate, linolenic acid, dihydrofuran, dihydropyran, acrylonitrile, N-vinylpyrrolidone. Most preferred are hydrocarbon compounds having two or more aliphatic unsaturated groups, such as 1,5-hexadiene, divinylbenzene or divinylether.

The term "silanes" encompasses compounds containing one silicon atom or two or more silicon atoms bond to each other.

The term "siloxanes" encompasses compounds contain chains of alternating silicon and oxygen atoms, for example, —Si—O—Si—, —Si—O—Si—O—, —Si—O—Si—O—Si—O— (wherein substituents of the silicon atom are omitted), and so on.

Silanes having one or more aliphatic unsaturated groups preferably have the formula (X):

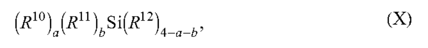

$$(R^{10})_a(R^{11})_bSi(R^{12})_{4-a-b}, \quad (X)$$

wherein $R^{12}$ is a group of the following formula (XI):

(XI)

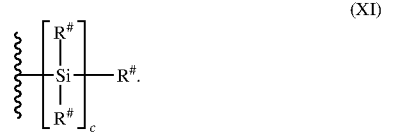

In formula (X), $R^{10}$ represents an aliphatic unsaturated group, a fluoro atom, a linear, branched or cyclic alkyl group, an aryl group, which alkyl or aryl group may optionally be substituted with one or more groups selected from a hydroxyl group, an alkoxy group or a halogen atom (F, Cl, Br or I), provided that at least one $R^{10}$ represents an aliphatic unsaturated group; $R^{11}$ represents a chloro, bromo or iodo atom, an alkyl-, aryl- or arylalkyl-oxy group, or an alkyl-, aryl- or arylalkyl-acyloxy group; a represents 0 or an integer of from 1 to 3, and b represents 0 or an integer of 1 to 3, provided that the sum of a and b is at most 4.

In formula (XI), $R^{\#}$ represents $R^{10}$ or $R^{11}$ as defined above for formula (X), and c is an integer of from 1 to 7, preferably an integer of from 1 to 4, and most preferably c is 1 or 2.

For $R^{11}$ of formula (X), the alkyl-, aryl- or arylalkyl-oxy groups or -acyloxy groups are preferably selected from linear $C_{1-6}$, branched or cyclic $C_{3-6}$ alkyl, $C_{6-10}$ aryl or $C_{7-16}$ arylalkyl oxy groups or -acyloxy groups. For example, preferred alkyl-, aryl- or arylalkyl-oxy groups are methoxy, ethoxy, propoxy such as isopropoxy, butoxy such as tert-butoxy, phenoxy, benzyloxy, and preferred alkyl-, aryl- or arylalkyl-acyloxy groups are acetoxy, propionoxy such as iso-propionoxy, and benzoyloxy.

In formula (X), each of $R^{10}$, $R^{11}$ and $R^{12}$ is bond to the silicon atom by means of a single bond.

Preferably, in formula (X), the sum of a and b is 4, most preferably a is 4. That is, preferred silanes of formula (X) are monosilanes.

Linear or branched organic siloxanes having one or more aliphatic unsaturated groups preferably have the following formula (XII):

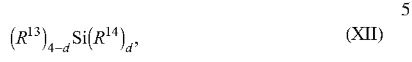

(XII)

wherein $R^{13}$ is a group of the following formula (XIII):

(XIII)

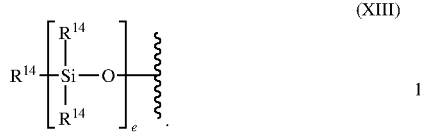

In formula (XII) and (XIII), the $R^{14}$, which may be the same or different, independently represent an aliphatic unsaturated group, a linear, branched or cyclic alkyl group, an aryl group, which alkyl or aryl group may optionally be substituted with one or more groups selected from a hydroxyl group, an alkoxy group or a halogen atom (F, Cl, Br or I), provided that at least one $R^{14}$ represents an aliphatic unsaturated group, d is 0 or an integer of from 1 to 3, and e represents an integer of from 1 to 3000.

In linear organic siloxanes of formula (XII), d is 2 or 3, and in branched organic hydrosiloxanes of formula (XII), d is 0 or 1. Linear organic hydrosiloxanes of formula (XII) with d being 2 or 3 are preferred, and most preferred are linear organic hydrosiloxanes of formula (XII) with d being 3.

Preferably, in organic siloxanes of formula (XII), $R^{14}$, which may be the same or different, independently represent an aliphatic unsaturated group, a linear $C_{1-18}$, $C_{3-18}$ branched or $C_{3-12}$ cyclic alkyl group, a $C_{6-12}$ aryl group, which alkyl or aryl groups may optionally be substituted with one or more groups selected from a hydroxyl group, a $C_{1-4}$ alkoxy group or a halogen atom (F, Cl, Br or I), d is 0 or an integer of from 1 to 3, and e represents an integer of from 1 to 1000. More preferably $R^{14}$, which may be the same or different, independently represent an aliphatic unsaturated group selected from linear $C_{3-5}$ or branched or cyclic $C_{3-6}$ alkenyl group, which is optionally substituted with one or more halogen atom(s) (F, Cl, Br, I), a linear $C_{1-9}$, $C_{3-9}$ branched alkyl group, a $C_{5-10}$ cycloalkyl group or a $C_{6-10}$ aryl group, d is 2 or 3, and e represents an integer of from 2 to 500. Even more preferably, $R^{14}$, which may be the same or different, independently represent an aliphatic unsaturated group selected from the group consisting of vinyl, propenyl, chlorovinyl, and 5-hexenyl, a linear $C_{1-4}$ or $C_{3-4}$ branched alkyl group, a cyclopentyl group, a cyclohexyl group or a phenyl group, d is 3, and e represents an integer of from 3 to 100. Most preferably, $R^{14}$, which may be the same or different, independently represent an aliphatic unsaturated group in the form of vinyl or chlorovinyl, or a linear $C_{1-4}$ or $C_{3-4}$ branched alkyl group, d is 3, and e represents an integer of from 10 to 50.

In formula (XIII), units $—(R^{14})_2Si—O—$ may be repeated in separate blocks of different units $—(R^{14})_2Si—O—$ for $e_1$-, $e_2$-, $e_3$-, $e_4$-times, and so on, wherein e is the sum of $e_1$, $e_2$, $e_3$, $e_4$, and so. For example, a first block may be $[—(R^{14})_2Si—O—]_{e1}$ wherein the $R^{14}$ are the same, a second block $[—(R^{14})_2Si—O—]_{e2}$ wherein the $R^{14}$ are different, and so on.

Most preferred are linear organic siloxanes, notably vinyl-group-containing polymethylsiloxanes, of the following formula (XII'):

(XII')

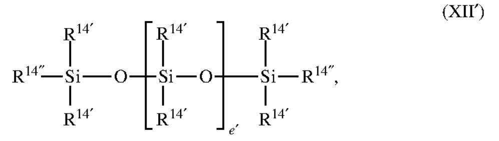

wherein the $R^{14'}$, which may be the same or different, independently represent a linear $C_{1-4}$ or $C_{3-4}$ branched alkyl group, a cyclopentyl group, a cyclohexyl group or a phenyl group, the $R^{14''}$, which may be the same or different, independently represent an aliphatic unsaturated group selected from linear $C_{2-6}$ or branched or cyclic $C_{3-6}$ alkenyl group, which is optionally substituted with one or more halogen atom(s) (F, Cl, Br, I), and e' represents an integer of from 30 to 500. More preferably, in formula (XIII'), the $R^{14'}$ are the same and represent a linear $C_{1-4}$ or $C_{3-4}$ branched alkyl group, the $R^{14''}$ are the same and represent an aliphatic unsaturated group selected from the group consisting of vinyl, propenyl, chlorovinyl, and 5-hexenyl, and e' represents an integer of from 50 to 400, most preferably $R^{14'}$ are the same and represent a methyl group, the $R^{14''}$ are the same and represent an aliphatic unsaturated group in the form of vinyl or chlorovinyl, and e' represents an integer of from 80 to 400.

Cyclic organic silanes having one or more aliphatic unsaturated groups preferably have the following formula (XIV):

(XIV)

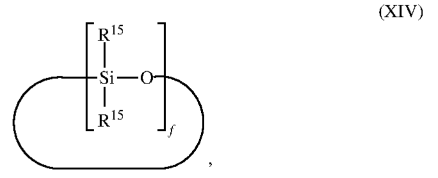

wherein $R^{15}$ has the same meaning as defined above for $R^{13}$ or $R^{14}$ of formula (XII), preferably $R^{15}$ has the same meaning as defined above for $R^{14}$ of formula (XII), and f is an integer of from 3 to 18, more preferably 4 to 12, most preferably 5 to 10.

In formula (XIII), the oval line indicates a cyclic bonding.

Preferably, in any one of the above described formulae (X), (XII) and (XIV), at most a tenth of all $R^{14}$ or $R^{15}$ groups represent an aliphatic unsaturated group.

It is preferred that the compound according to (i) has two or more aliphatic unsaturated groups.

Preferably, the compound according to (i) is a linear or branched organic siloxane of formula (XII), more preferably a linear organic siloxane of formula (XII) with d being 2 or 3, and most preferably a linear organic siloxane of formula (XII').

It is preferred that the compound according to (i) is contained in the present dental impression material in an amount of from 5 to 80 weight percent of the entire composition, more preferably, 10 to 60 weight percent, most preferably 15 to 45 weight percent. Furthermore, the present dental impression material comprises (ii) a compound containing at least one silicon-bonded hydrogen atom. The dental impression material may comprise one or a mixture of two or more compound(s) containing at least one silicon-bonded hydrogen atom (ii).

The compound(s) containing at least one silicon-bonded hydrogen atom (ii) may be organic or inorganic silanes, or linear, branched or cyclic organic hydrosiloxanes.

The term "silanes" encompasses compounds containing one silicon atom or two or more silicon atoms bond to each other.

The term "organic hydrosiloxanes" encompasses compounds contain chains of alternating silicon and oxygen atoms, for example, —Si—O—Si—, —Si—O—Si—O—, —Si—O—Si—O—Si—O— (wherein substituents of the silicon atom are omitted), and so on, and comprising at least one organic moiety in the form of a hydrocarbon group.

Organic or inorganic silanes containing at least one silicon-bonded hydrogen atom preferably have the following formula (XV):

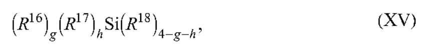

wherein $R^{18}$ is a group of the following formula (XVI):

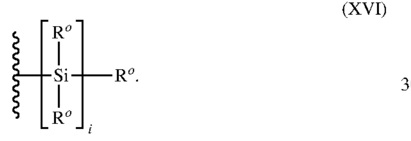

In formula (XV), the $R^{16}$, which may be the same or different, independently represent a hydrogen atom, a fluoro atom, a linear, branched or cyclic alkyl group, an aryl group, which alkyl or aryl group may optionally be substituted with one or more groups selected from a hydroxyl group, an alkoxy group or a halogen atom (F, Cl, Br or I), provided that at least one $R^{16}$ represents a hydrogen atom; $R^{17}$ represents a chloro, bromo or iodo atom, alkyl-, aryl- or arylalkyl-oxy group, an alkyl-, aryl- or arylalkyl-acyloxy group; g represents an integer of from 1 to 4, h represents 0 or an integer of from 1 to 3, provided that the sum of g and h is at most 4.

In formula (XVI), $R^{\circ}$ represents $R^{16}$ or $R^{17}$ as defined above for formula (XV), and i is an integer of from 1 to 7, preferably 1 or 2. Preferably, in formula (XV), the sum of g and h is 2 to 4, more preferably 3. Most preferably, in formula (XV), the sum of g and h is 3 and i represents 1.

In formula (XV), each of $R^{16}$, $R^{17}$ and $R^{18}$ is bond to a silicon atom by means of a single bond.

For $R^{17}$ of formula (XV) and (XVI), the alkyl-, aryl- or arylalkyl-oxy groups or -acyloxy groups are preferably selected from linear $C_{1-6}$, branched or cyclic $C_{3-6}$ alkyl, $C_{6-10}$ aryl or $C_{7-16}$ arylalkyl oxy groups or -acyloxy groups. For example, preferred alkyl-, aryl- or arylalkyl-oxy groups are methoxy, ethoxy, propoxy such as isopropoxy, butoxy such as tert-butoxy, phenoxy, benzyloxy, and preferred alkyl-, aryl- or arylalkyl-acyloxy groups are acetoxy, propionoxy such as iso-propionoxy, and benzoyloxy.

In inorganic silanes, in formula (XV), $R^{16}$ represents a hydrogen atom or a fluoro atom, and $R^{17}$ represents Cl, Br or I. That is, inorganic silanes to not contain organic hydrocarbon groups such as alkyl or aryl groups. Suitable inorganic silanes are for example dibromosilane, trichlorsilane, pentachlorodisilane or heptachlorotrisilane.

Linear or branched organic hydrosiloxanes containing at least one silicon-bonded hydrogen atom preferably have the following formula (XVII):

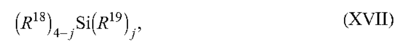

wherein $R^{18}$ is a group of the following formula (XVIII):

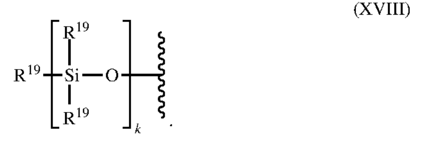

In formula (XVII) and (XVIII), the $R^{19}$, which may be the same or different, independently represent a hydrogen atom, a linear, branched or cyclic alkyl group, an aryl group, which alkyl or aryl group may optionally be substituted with one or more groups selected from a hydroxyl group, an alkoxy group or a halogen atom (F, Cl, Br or I), provided that at least one $R^{19}$ represents a hydrogen atom, j is 0 or an integer of from 1 to 3, and k represents an integer of from 1 to 3000.

In linear organic hydrosiloxanes of formula (XV), j is 2 or 3, and in branched organic hydrosiloxanes of formula (XVI), j is 0 or 1. Linear organic hydrosiloxanes of formula (XVII) with j being 2 or 3, are preferred, and most preferred are linear organic hydrosiloxanes of formula (XVII) with j being 3.

It is preferred that in organic hydrosiloxanes of formula (XVII), at most half of all $R^{19}$ represent a hydrogen atom.

Preferably, in in organic hydrosiloxanes of formula (XVII), $R^{19}$, which may be the same or different, independently represent a hydrogen atom, an linear $C_{1-18}$, $C_{3-18}$ branched or $C_{3-12}$ cyclic alkyl group, or a $C_{6-12}$ aryl group, which alkyl or aryl groups may optionally be substituted with one or more groups selected from a hydroxyl group, a $C_{1-4}$ alkoxy group or a halogen atom (F, Cl, Br or I), j is 0 or an integer of from 1 to 3, and k represents an integer of from 1 to 1000. More preferably $R^{19}$, which may be the same or different, independently represent a hydrogen atom, a linear $C_{1-9}$ or $C_{3-9}$ branched alkyl group, a $C_{5-10}$ cycloalkyl group or a $C_{6-10}$ aryl group, j is 2 or 3, and k represents an integer of from 2 to 500. Even more preferably, $R^{19}$, which may be the same or different, independently represent a hydrogen atom, a linear $C_{1-4}$ or $C_{3-4}$ branched alkyl group, a cyclopentyl group, a cyclohexyl group or a phenyl group, j is 3, and k represents an integer of from 3 to 100. Most preferably, $R^{19}$, which may be the same or different, independently represent a hydrogen atom, a linear $C_{1-4}$ or $C_{3-4}$ branched alkyl group, j is 3, and k represents an integer of from 10 to 50.

In formula (XVIII), units —$(R^{19})_2$Si—O— may be repeated in separate blocks of different units —(—$(R^{19})_2$Si—O— for $k_1$-, $k_2$-, $k_3$-, $k_4$-times, and so on, wherein k is the sum of $e_1$, $e_2$, $e_3$, $e_4$, and so.

For example, a first block may be $[—R^{19}SiH—O—]_{k1}$, a second block may be $[—(R^{19})_2Si—O—]_{k2}$ wherein the $R^{19}$ are the same, a third block $[—(R^{19})_2Si—O—]_{k3}$ wherein the $R^{19}$ are different, and so on.

Most preferred are linear organic hydrosiloxanes of the following formula (XVII'):

(XVII')

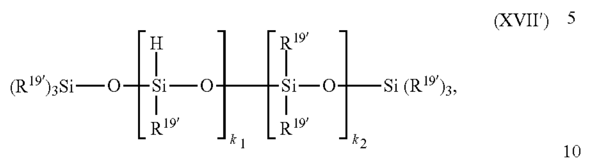

wherein $R^{19'}$, which may be the same or different, independently represent a linear $C_{1-4}$ or $C_{3-4}$ branched alkyl group, a cyclopentyl group, a cyclohexyl group or a phenyl group, $i_1$ represents an integer of from 3 to 50, and $i_2$ represents an integer of from 0 to 50. More preferably, in formula (XV'), $R^{19'}$ are the same and represent a linear $C_{1-4}$ or $C_{3-4}$ branched alkyl group, $k_1$ represents an integer of from 5 to 40, and $k_2$ represents an integer of from 5 to 45, most preferably $R^{19'}$ are the same and represent a methyl group, $k_1$ represents an integer of from 8 to 40, and $k_2$ represents an integer of from 10 to 30.

Cyclic organic hydrosilanes containing at least one silicon-bonded hydrogen atom preferably have the following formula (XIX):

(XIX)

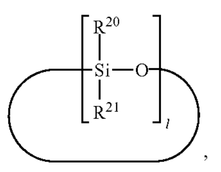

wherein $R^{20}$ has the same meaning as defined above for $R^{18}$ or $R^{19}$ of formula (XIX), preferably $R^{20}$ has the same meaning as defined above for $R^{19}$ of formula (XIX), and l is an integer of from 3 to 18, preferably l is an integer of from 4 to 14, more preferably l is an integer of from 6 to 10.

In formula (XIX), the oval line indicates a cyclic bonding.

In any one of the above-described formulae (XV), (XVII) and (XIX), not more than three hydrogen atoms are attached to any one of the silicon atom(s) of formulae (XV), (XVII) and (XIX).

It is preferred that the compound according to (ii) contains two or more silicon-bonded hydrogen atoms, which are preferably located at different silicon atoms.

Preferably, the compound according to (ii) is a linear or branched hydrosiloxanes of formula (XII), more preferably a linear organic hydrosiloxane of formula (XII) with j being 2 or 3, most preferably a linear organic hydrosiloxane of formula (XII').

It is preferred that the compound according to (ii) is contained in the present dental impression material in an amount of from 5 to 80 weight percent of the entire composition, more preferably, 10 to 60 weight percent, most preferably 15 to 45 weight percent.

It is preferred that the compound according to (i) has two or more aliphatic unsaturated groups, and the compound according to (ii) contains two or more silicon-bonded hydrogen atoms. This combination of two or multi-functional compounds according to (i) and (ii) renders possible the formation of a polymer formed by hydrosilylation reaction.

More preferably, in the combination of a compound according to (i) having two or more aliphatic unsaturated groups and a compound according to (ii) containing two or more silicon-bonded hydrogen atoms, at least one of the compounds according to (i) has three or more aliphatic unsaturated groups and/or at least one of compounds according to (ii) contains three or more silicon-bonded hydrogen atoms. This combination multi-functional compounds according to (i) and/or (ii) having three or more functional groups for hydrosilylation reaction render possible the formation of crosslinked polymer networks by hydrosilylation reaction.

In Scheme 1, hydrosilylation reaction between the compounds according to (i) and (ii) is exemplary shown for compounds of formula (XII") and (XVII'):

Scheme 1: Hydrosilylation reaction between compounds of formula (XI") and (XV')

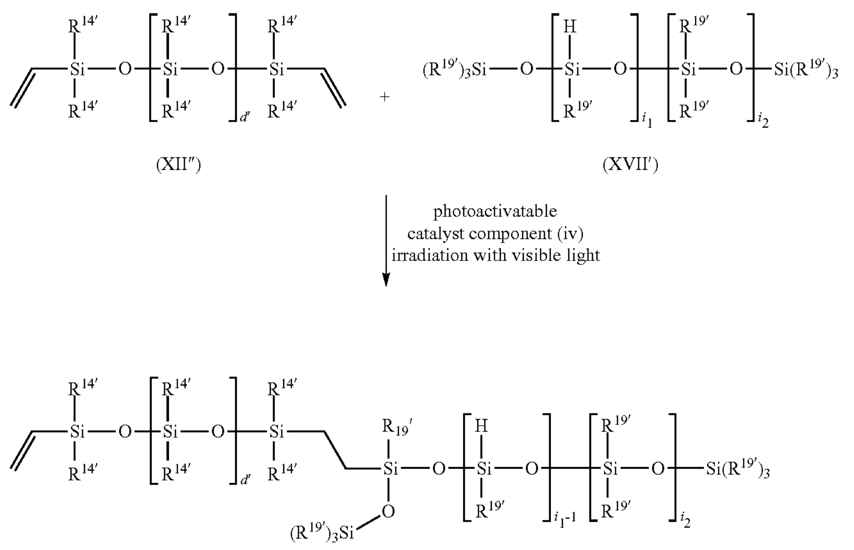

In Scheme 1, the $R^{14'}$, d', the $R^{19'}$, $i_1$ and $i_2$ have the same meaning as defined above for compounds of formula (XII") and (XVII'). Compound of formula (XII") is a compound of formula (XII') in which a vinyl group is selected for the aliphatic unsaturated group $R^{14''}$. It is understood that a combination of any compounds according to (i) and (ii) will undergo hydrosilylation reaction.

In Scheme 1, schematically, only a single hydrosilylation reaction between one aliphatic unsaturated group of formula (XII") and one silicon-bonded hydrogen atom of formula (XVII') is shown. However, it is understood that both aliphatic unsaturated groups of formula (XII") and further silicon-bonded hydrogen atoms of formula (XVII') will react with each other, whereby a macromolecule such as an oligomer or polymer is formed.

According to a preferred embodiment of the dental impression material according to the present invention, the compound having one or more aliphatic unsaturated groups of component (i) is a linear vinyl group-containing polymethylsiloxane having a molecular weight of more than 5000 Da, and wherein the retarder of component (v) is a cyclic vinyl-group-containing polymethylsiloxane having a molecular weight of at most 5000 Da.

(iii) The Particulate Filler

The present dental impression material comprises (iii) a particulate filler. The dental impression material may comprise one or a mixture of two or more particulate filler(s) (iii).

The particulate filler (iii) provides for a suitable adjustment of the rheological properties of the dental impression material in terms of viscosity or thixotropie, and for preventing shrinkage of the dental impression material. In addition, the particulate filler (iii) may provide for improved mechanical properties of the cured dental impression material, for example in terms of tensile strength and tear strength.

Preferably, the particulate filler (iii) is selected from oxides of silicone, aluminum, manganese or titanium, other metal oxides, glasses, and inorganic salts. More preferably, the particulate filler (iii) is selected from silicas, most preferably from silicas selected from the group consisting of crystalline silicone dioxide, such as pulverized quartz, amorphous silicone dioxides, such as diatomaceous earth, and fumed silica, such as Cab-o-Sil® by Cabot corporation, Aerosil® by Evonik corporation, or HDK® by Wacker Chemie corporation.

The particulate filler (iii) may be partially or fully surface treated with one or more silanating agents in the form of e.g. halogenated silanes or silazides.

For a suitable adjustment of the rheological properties of the dental impression material, it is preferred that the particulate filler (iii) has a maximum particle diameter less than about 100 μm and an average particle diameter less than about 10 μm. The filler may have a unimodal or polymodal (e.g., bimodal) particle size distribution.

In addition to the particle diameter, the rheological properties of the dental impression material may further be suitably set by the selection of the BET surface area of the particulate filler (iii). Preferably, the particulate filler (iii) has a BET surface area of at least 20 $m^2/g$, preferably 25 to 600 $m^2/g$, more preferably 40 to 500 $m^2/g$, most preferably 50 to 400 $m^2/g$.

Preferably, the particulate filler (iii) is contained in the present dental impression material in an amount of at most 50 weight percent, more preferably from 5 to 45 weight percent of the entire composition, most preferably from 15 to 40 weight percent.

(iv) The Photoactivatable Metal Catalyst Component

The present dental impression material comprises (iv) a photoactivatable metal catalyst component. The dental impression material may comprise one or a mixture of two or more photoactivatable catalyst component(s) (iv).

According to a preferred embodiment, the photoactivatable metal catalyst component is a transition metal compound containing a transition metal selected from the group of Pt, Pd, Rh, Co, Ni, Ir and Ru, preferably the transition metal compound is selected from platinum (II)acetylacetonate and $(Cp)Pt(C_{1-6}alkyl)_3$, wherein Cp represents a cyclopentadienyl group which may be substituted by one or more alkyl groups, preferably a Karstedt catalyst.

The photoactivatable metal catalyst component (iv) provides for initiation of a hydrosilylation reaction between the compounds according to (i) to (ii). In case an aliphatic unsaturated bond of a compound according to (i) is asymmetrically substituted, the anti-Markovnikov addition product is formed, that is the compound according to (ii) adds to the less substituted carbon atom of the aliphatic unsaturated group of the compound according to (i).

It is preferred that the photoactivatable metal catalyst component (iv) has a sufficient storage stability when incorporated into the dental impression material, in particular when incorporated into one-pack dental impression material. A preferred storage stability may for example be that the dental impression material keeps its characteristics of an advantageous efficiency in terms of a higher polymerisation rate and a higher final conversion rate even after a long storage time, e.g. of about 2 month.

The photoactivatable metal catalyst component (iv) is a transition metal compound containing Pt.

The transition metal compound is preferably platinum (0)-1,3,divinyl-tetramethyldisiloxane complex solution in vinyl terminated poly(dimethylsiloxane) (Karstedt's catalyst).

It is preferred that the photoactivatable catalyst component (iv) is contained in the present dental impression material in an amount of up to 5.0 weight percent of the entire composition, more preferably, 0.1 to 4.0 weight percent.

(v) Retarder

The dental impression material contains a retarder. The retarder is used for increasing the working time. The retarder may be a silicone compound having vinyl groups linked to a silicon atom. A retarder preferably has a molecular weight in the range of from 100 to 5000 Da. More preferably, the retarder has a molecular weight in the range of from 150 to 4000 Da. A preferred retarder is a polymer of vinyl methyl siloxane. Preferably, the retarder is a cyclic or linear oligomeric or polymeric alkyl vinyl siloxane, more preferably a cyclic oligomeric or polymeric methyl vinyl siloxane.

Although the retarder may be considered as a compound having one or more aliphatic unsaturated groups, the retarder is different from a compound having one or more aliphatic unsaturated groups according to component (i). Specifically, the molecular weight of the retarder is not high enough so as to allow the preparation of a useful dental impression material without a compound of component (i). The retarder acts as a chain stopper and temporarily prevents polymerization of compounds having one or more aliphatic unsaturated groups according to component (i). The retarder continues to polymerize until it is completely consumed and then the compound having one or more aliphatic unsaturated groups according to component (i) polymerize causing the dental impression material to set.

(vi) The Photosensitizer

Preferably, the photosensitizer is a 1,2-diketone, a 1,3-diketone, a phosphine oxide, thioxanthone or a derivative thereof, or a polycyclic aromatic hydrocarbon or a derivative thereof. More preferably, the photosensitizer is a 1,2-diketone, anthracene or a derivative thereof substituted in the 2-position, benzo[a]pyrene, anthracene or a derivate thereof substituted in 9 and 10 position and optionally in 2 position, or benzo[a]pyrene. Even more preferably, the photosensitizer is camphor quinone, benzyl, 2-isopropylthioxanthone (ITX), 2-chlorothioxanthone, anthracene, 9,10-dihalogeno-, dialkyl-, -dialkoxy-anthracene, optionally substituted with a linear or branched $C_{1-4}$ alkyl group in 2-position. Most preferably, the photosensitizer is camphor quinone, benzyl, 2-isopropylthioxanthone (ITX), 2-chlorothioxanthone, anthracene, 9,10-dibromo-, -dichloro-, dimethyl-, -diethoxy-anthracene, optionally substituted with a methyl or ethyl group in 2-position Two-Pack or Multi-Pack Composition The dental impression material according to the present invention may be a two-pack or a multi-pack dental impression material.

The term "two-pack" as used herein means that all components of the dental impression material are comprised in two single packs.

The term "multi-pack" as used herein means that the components of the dental impression material are comprised in a multitude of separate packs. For example, a first pack of components is comprised in a first pack, while as second pack of components is comprised in a second pack, a third pack of components may be comprised in a third pack, a fourth pack of components may be comprised in a fourth pack, and so on.

Preferably, the dental impression material is a two-pack dental impression material.

For the two-pack dental impression material, it is preferred that the first pack comprises for example the components according to (i), (ii) and (iii), and a second pack comprises the photoactivatable catalyst component (iv). The photosensitizer according to (v) may be comprised in the first or the second pack, preferably it is comprised in the first pack.

Use of the Dental Impression Material and Method for Preparing a Dental Impression The present dental impression material as described above may be used for the preparation of a dental impression.

The present invention further provides a method for preparing a dental impression, which method comprises (a) providing a dental impression material as described above;

(b) taking an impression of a dental structure;

(c) curing the dental impression material with light having a wavelength in the range of 400-800 nm.

Preferably, step (b) is carried out by placing a container filled with the present dental impression material over the sample to be impressed, for example dental arches. Then, in step (c), the dental impression material is cured by a suitable light source, whereby a negative imprint of e.g. the hard teeth and soft tissues is obtained. Preferably, in step (c), for curing, a light source being centered at a wavelength which wavelength within the range of 200 to 800 nm is applied, more preferably within the range of 350 to 600 nm. Alternatively or additionally, in step (c), a light source provides an irradiance of at least 500 mW/cm$^2$. It is particularly preferred that in step (c), a blue dental light emitting diode (LED) is used as light source, which is preferably centred within a range of 350 to 600 nm, more preferably centred at 477 nm, and which provides an irradiance of from 600 to 1200 mW/cm$^2$. Most preferred is a light source in the form of the blue dental LED SmartLite® Focus from Dentsply centred at 477 nm and providing an irradiance of 800 to 1100 mW/cm$^2$.

According to the present invention, an additional two-part chemically curable impression material is not required for preparing a dental impression.

The invention will now be further illustrated by the following Examples. Hereinafter, the present invention will be described in further detail with the reference to examples. The present invention is not limited to the examples described below. The following abbreviations are used hereinafter.

EXAMPLES

[Photosensitizer]

ITX: 2-Isopropylthioxanthone

CPTX: 1-Chloro-4-propoxy-9H-thioxanthen-9-one

Examples 1 to 5 and Comparative Example 1 to 4

In each example, the base resin as well as the catalyst comprising resin having respectively the compositions shown in Table 1 were mixed with a spatula on a wax-coated paper sheet in the given ratio for 30 seconds. Afterwards, the mixture was cured thermally or by means of a lamp (ultraviolet lamp, 405 nm). When examine the setting behavior of the resin-mixture at 37° C. the sample was transferred from the wax-coated paper sheet to a preheated and temperature controlled metal plate. The setting time was considered as the time at which the material does not stick on the spatula anymore. Therefore, the spatula was given on the surface of the mixture in a suitable interval.

[Photochemical Setting]

For photochemical curing an irradiation source having an emission maximum at 405 nm and a light intensity of 600 mW/cm$^2$ was used. The distance between the lamp and the resin mixture was hold constant at 1 cm. The results are shown in the following Table 1.

TABLE 1

| | | | Example 1 MYO 1-19-1-a/ MYO 1-47-1-b | Example 2 MYO 1-46-1-e/ MYO 1-47-1-b | Example 3 MYO 1-41-1-t/ MYO 1-41-1-e | Example 4 MYO 1-41-1-t/ MYO 1-41-1-k | Example 5 MYO 1-41-1-t/ MYO 1-41-1-m | Comparative Example for 1 and 2 MYO 1-09-1-a/ MYO 1-41-1-b | Comparative Example for 3 MYO 1-09-1-a/ MYO 1-41-1-e | Comparative Example for 4 MYO 1-09-1-a/ MYO 1-41-1-k | Comparative Example for 5 MYO 1-09-1-a/ MYO 1-41-1-m |
|---|---|---|---|---|---|---|---|---|---|---|---|
| Base Resin | Silopren H 60 | | 59 | 59.92 | 59.03 | 59.03 | 59.03 | 59.29 | 59.29 | 59.29 | 59.29 |
| | Silopren P 300 | | 23.18 | 22.60 | 22.26 | 22.26 | 22.26 | 23.30 | 23.30 | 23.30 | 23.30 |
| | Silopren AC 1905 | | 17.32 | 16.96 | 16.71 | 16.71 | 16.71 | 17.42 | 17.42 | 17.42 | 17.42 |
| | ITX | | 0.5 | — | 2.0 | 2.0 | 2.0 | — | — | — | — |
| | CPTX | | — | 0.52 | — | — | — | — | — | — | — |
| | Σ | | 100.00 | 100.00 | 100.00 | 100.00 | 100.00 | 100.00 | 100.00 | 100.00 | 100.00 |
| Catalyst Resin | Silopren H 60 | | 63.98 | 63.98 | 64.14 | 62.70 | 62.53 | 63.98 | 64.14 | 62.70 | 62.53 |
| | Silopren P 300 | | 34.29 | 34.29 | 34.95 | 34.17 | 34.07 | 34.29 | 34.95 | 34.17 | 34.07 |
| | Karstedt catalyst solution | | 1.47 | 1.47 | 0.51 | 3.03 | 3.0 | 1.47 | 0.51 | 3.03 | 3.0 |
| | Retarder Silicone | | 0.26 | 0.26 | 0.4 | 0.1 | 0.4 | 0.26 | 0.4 | 0.1 | 0.4 |
| | Σ | | 100.00 | 100.00 | 100.00 | 100.00 | 100.00 | 100.00 | 100.00 | 100.00 | 100.00 |
| Base-/ Catalyst resin ratio | | | 1/1 | 1/1 | 1/1 | 1/1 | 1/1 | 1/1 | 1/1 | 1/1 | 1/1 |
| Curing time [min] | thermal | ambient temperature | 5.5 | 5.5 | 20.5 | 1 | 3.6 | 5.5 | 20.5 | 1 | 3.6 |
| | | 37° C. | 1.5 | 1.5 | 6.4 | 0.5 | 1.16 | 1.5 | 6.4 | 0.5 | 1.16 |
| | photochemical | ambient temperature | 0.8 | 0.66 | 2.8 | 0.16 | 0.5 | 1.66 | 7.55 | 0.5 | 1.1 |
| | | 37° C. | 0.5 | 0.5 | 2.66 | 0.12 | 0.2 | 1 | 4.1 | 0.33 | 0.75 |

As shown by the Examples and Comparative Examples, the combination of components (i) to (vi) may be hardened by irradiation of light, whereby the curing speed may be adjusted by suitably selecting type and amount of a photosensitizer and a retarder for a Karstedt catalyst. Moreover, despite the high reactivity, a dental impression material has a high storage stability.

The invention claimed is:

1. A curable dental impression material, comprising:

(i) a compound having one or more aliphatic unsaturated groups and in a range of from 15 to 45 weight percent of the material;

(ii) a compound containing at least one silicon-bonded hydrogen atom and not having more than three hydrogen atoms attached to any one silicon atom and in a range of from 15 to 45 weight percent of the material;

(iii) a particulate filler and in a range of from 15 to 40 weight percent of the material;

(iv) a metal catalyst component consisting of platinum (0)-1,3-divinyl-tetramethyldisiloxane complex solution in vinyl terminated poly(dimethylsiloxane) in a range of from 0.1 to 4.0 weight percent of the material;

(v) a retarder comprising a cyclic vinyl-group-containing polymethylsiloxane having a molecular weight of at most 5000 Da, and (vi) a photosensitizer comprising 2-isopropylthioxanthone or 1-Chloro-4-propoxy-9H-thioxanthen-9-one ranging from about 0.25 wt % to about 1.0 wt % of the material;

wherein the retarder is different from the compound having one or more aliphatic unsaturated groups according to component (i).

2. The curable dental impression material according to claim 1, wherein the dental impression material further comprises a stabilizer.

3. The curable dental impression material according to claim 1, wherein the compound having one or more-aliphatic, unsaturated groups of component (i) is a linear vinyl group-containing polymethylsiloxane having a molecular weight of more than 5000 Da.

4. A method for preparing a dental impression, said method comprising:

(a) providing the curable dental material of claim 1, (b) taking an impression of a dental structure; and (c) curing the dental impression material with light having a wavelength in the range of 200 to 800 nm.

5. The curable dental impression material according to claim 1 wherein the metal catalyst component is in a range of from about 0.25 to about 1.5 weight percent of the material.

6. The curable dental impression material according to claim 1, wherein the photosensitizer is 1-Chloro-4-propoxy-9H-thioxanthen-9-one.

7. A curable dental impression material, comprising:

(i) a compound having one or more aliphatic unsaturated groups and in a range of from 15 to 45 weight percent of the material;

(ii) a compound containing at least one silicon-bonded hydrogen atom and not having more than three hydrogen atoms attached to any one silicon atom and in a range of from 15 to 45 weight percent of the material;

(iii) a particulate filler and in a range of from 15 to 40 weight percent of the material;

(iv) a metal catalyst component consisting of platinum (0)-1,3-divinyl-tetramethyldisiloxane complex solution in vinyl terminated poly(dimethylsiloxane) in a range of from 0.1 to 4.0 weight percent of the material;

(v) a retarder comprising a cyclic vinyl-group-containing polymethylsiloxane having a molecular weight of at most 5000 Da, and (vi) a photosensitizer comprising 1-Chloro-4-propoxy-9H-thioxanthen-9-one;

wherein the retarder is different from the compound having one or more aliphatic unsaturated groups according to component (i).

8. The curable dental impression material of claim 7, wherein the photosensitizer ranges from about 0.25 wt % to about 1.0 wt % of the material.

9. The curable dental impression material according to claim 7, wherein the particulate filler has a polymodal particle size distribution.

10. The curable dental impression material according to claim 7, wherein the compound having one or more-aliphatic, unsaturated groups of component (i) is a linear vinyl group-containing polymethylsiloxane having a molecular weight of more than 5000 Da.

* * * * *